(12) United States Patent
Marshall (10) Patent No.: US 7,036,169 B2
(45) Date of Patent: May 2, 2006

(54) EXTREMITY POSITIONER

(76) Inventor: Mabel E. Marshall, 24650 Sussex Hwy., Bridgeville, DE (US) 19933

( * ) Notice: Subject to any disclaimer, the term of this patent is extended or adjusted under 35 U.S.C. 154(b) by 0 days.

(21) Appl. No.: 10/295,590

(22) Filed: Nov. 15, 2002

(65) Prior Publication Data

US 2004/0093673 A1    May 20, 2004

(51) Int. Cl.
*A61B 6/04* (2006.01)
*A47C 20/02* (2006.01)

(52) U.S. Cl. .................... 5/650; 5/651; 378/208

(58) Field of Classification Search .............. 5/650, 5/630, 648, 652, 655.9, 657, 922, 649, 651; 378/208, 209; 128/870, 882
See application file for complete search history.

(56) References Cited

U.S. PATENT DOCUMENTS

| | | | | |
|---|---|---|---|---|
| 3,521,876 A * | 7/1970 | Smith | ...... | 378/208 |
| 3,639,927 A * | 2/1972 | Munch | ...... | 5/651 |
| 3,783,863 A * | 1/1974 | Kliever | ...... | 128/847 |
| 3,851,644 A * | 12/1974 | Slagle | ...... | 128/870 |
| 4,181,297 A * | 1/1980 | Nichols | ...... | 378/208 |
| 4,232,681 A * | 11/1980 | Tulaszewski | ...... | 378/208 |
| 4,407,277 A * | 10/1983 | Ellison | ...... | 378/208 |
| 4,443,005 A * | 4/1984 | Sugarman et al. | ...... | 378/208 |
| 4,502,170 A * | 3/1985 | Morrow | ...... | 5/632 |
| 4,700,373 A * | 10/1987 | Miller | ...... | 378/177 |
| 4,840,362 A * | 6/1989 | Bremer et al. | ...... | 5/632 |
| 4,854,305 A * | 8/1989 | Bremer | ...... | 128/870 |
| 5,025,802 A * | 6/1991 | Laico et al. | ...... | 128/882 |
| 5,081,665 A * | 1/1992 | Kostich | ...... | 5/637 |
| 5,125,123 A * | 6/1992 | Engle | ...... | 128/882 |
| 5,329,934 A * | 7/1994 | Bowman | ...... | 5/603 |
| D360,796 S * | 8/1995 | Goldado | ...... | 5/651 |
| 5,454,993 A * | 10/1995 | Kostich | ...... | 264/46.4 |
| 5,479,471 A * | 12/1995 | Buckland | ...... | 378/208 |
| 5,484,393 A * | 1/1996 | McCoy | ...... | 602/6 |
| 5,665,059 A * | 9/1997 | Klearman et al. | ...... | 128/882 |
| 5,687,742 A * | 11/1997 | Johnson | ...... | 5/650 |
| 5,746,218 A * | 5/1998 | Edge | ...... | 128/882 |
| 5,790,998 A * | 8/1998 | Crescimbeni | ...... | 128/882 |
| 6,032,669 A * | 3/2000 | Klein | ...... | 128/882 |
| 6,163,902 A * | 12/2000 | Mollette et al. | ...... | 5/601 |
| 6,234,173 B1 * | 5/2001 | Hajianpour | ...... | 128/882 |
| 6,357,066 B1 * | 3/2002 | Pierce | ...... | 5/710 |
| 6,637,056 B1 * | 10/2003 | Tybinkowski et al. | ...... | 378/209 |
| 6,726,642 B1 * | 4/2004 | Danielsson et al. | ...... | 602/5 |
| 2003/0200971 A1 * | 10/2003 | Rastegar et al. | ...... | 128/870 |

* cited by examiner

*Primary Examiner*—Michael Safavi
(74) *Attorney, Agent, or Firm*—Porter Wright Morris & Arthur, LLP (57) ABSTRACT

A device for positioning at least one extremity of a patient during medical imaging is disclosed. The device comprises a radiotranslucent platform, at least one radiotranslucent support object, and at least one attachment to releasably secure the support object to the platform.

17 Claims, 8 Drawing Sheets

Figure 6B

# EXTREMITY POSITIONER

BACKGROUND

Diagnosing disease or injury of the lower extremities is challenging due to the complex anatomy of the lower leg, ankle, and foot. Medical imaging techniques, such as x-ray, magnetic resonance imaging (MRI), computed tomography (CT), fluoroscopy, and ultrasound provide images of soft tissue, bone, and vasculature that are useful in diagnosing illnesses and injuries in the lower extremities. Images are used to evaluate a patient's knee, ankle or foot for a wide range of problems, including fracture, fusion of joints, arthritis, joint degeneration, localization of a foreign body, determination of chronic pain, and the like.

Body positioning is important in obtaining specific planar views in imaging the lower extremities. Because the anatomy of the lower extremities is complex, evaluation of an image of the area is improved by specific positioning the knee, ankle, and foot during the creation of the image. Depending on the nature of the problem, an injury to the ankle may be evaluated using an image of the foot in either dorsiflexion (toe pointed up) or plantar flexion (toe pointed down). Patients are routinely scanned with the ankle in about 10 degrees to about 20 degrees of plantar flexion. Such a position is generally more comfortable for the patient and provides more consistent visualization of lateral ligamentous anatomy.

Depending on the illness or injury, a foot may be imaged in the oblique axial plane (i.e., parallel to the long axis of the metatarsal bones), oblique coronal plane (i.e., perpendicular to the long axis of the metatarsals), and/or oblique sagittal plane. Ankle imaging includes axial, coronal, and sagittal planes. For tendon abnormalities, the ankle may be positioned to provide an image of the tendons across the malleoli.

The simultaneous scanning of both lower extremities provides comparative images to aid in the diagnosis of injuries or illnesses. By scanning both normal and injured extremities, the images of the structures may be compared. Such simultaneous scanning is useful in evaluating tendon or ligamentous disorders, where the extremities are positioned at nearly the same angle of inflection for comparison.

Specific disorders of the lower extremities are routinely imaged in predetermined positions for assessment. For example, for subtalar (rotational) instability, coronal imaging is performed with the ankle placed in a plantar flexion position; in identifying subluxation (misalignment) of the bony joint or peroneal tendons, an axial image is obtained with the ankle in a dorsiflexion position. Evaluation of partial tears of the tendons and ligaments, as well as verifying anterior and posterior bony displacement routinely require the need for sagittal reconstructions to accentuate the fat plane between the tendons and to allow better visualization of joints and ligaments.

Medical imaging techniques currently require that a patient remain motionless in a specific position during the imaging. For lower extremity imaging, a patient must maintain one or both ankles at a predetermined angle. Depending on the image desired, a scan might take from about 10 to about 15 minutes per view (axial or coronal). Maintaining a given position without moving for that length of time proves difficult for many patients. In order to assist a patient in maintaining the desired angle for imaging one or both of the lower extremities, pillows or cushions are sometimes placed under the patient's knees. Such methodologies usually result in difficult to reproduce positioning, slippage, and non-standardized angles of flexion.

Some imaging facilities attach the pillow or cushion to the patient, for example, by using surgical tape, to attempt to maintain the patient in the correct position and reduce slippage. When patients are unable to relax the ankle to allow the foot to rest flat when the knee is bent, some imaging facilities immobilize such patients by taping the patient's toes to the table to create the angle and prevent slippage.

Patients that present with an illness or injury to the lower extremity are usually in pain, and do not tolerate medical imaging positioning well for long periods of time. Movement during imaging results in poor diagnostic quality and necessitates repeated imaging, which is a burden to the patient as well as causing scheduling problems in busy imaging centers. Repeat images also adds to the amount of radiation to which the patient is exposed. Removal of tape is often painful for a patient. Accordingly, a need exists for improved positioning devices and methods.

SUMMARY

A device for positioning at least one extremity of a patient during medical imaging is disclosed. The device comprises a radiotranslucent platform, at least one radiotranslucent support object, and at least one attachment to releasably secure the support object to the platform.

DESCRIPTION

A device for positioning at least one extremity of a patient during medical imaging comprising a radiotranslucent platform, at least one radiotranslucent support object, and at least one attachment to releasably secure the support object to the platform is disclosed.

Figure 1:
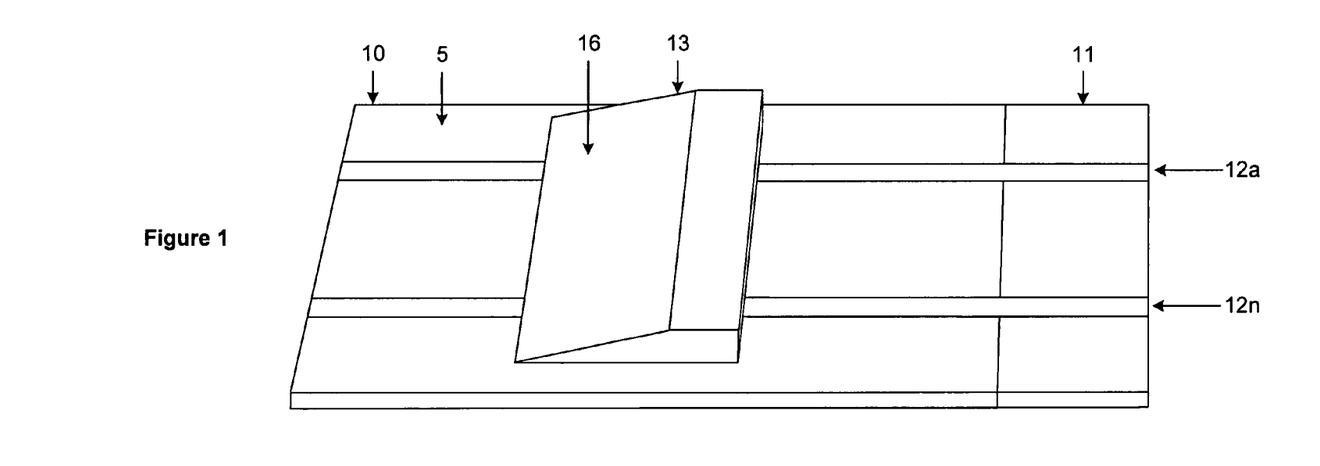
FIG. 1 is a perspective top view showing an example of a platform with an extension and a support object.
Figure 1A:
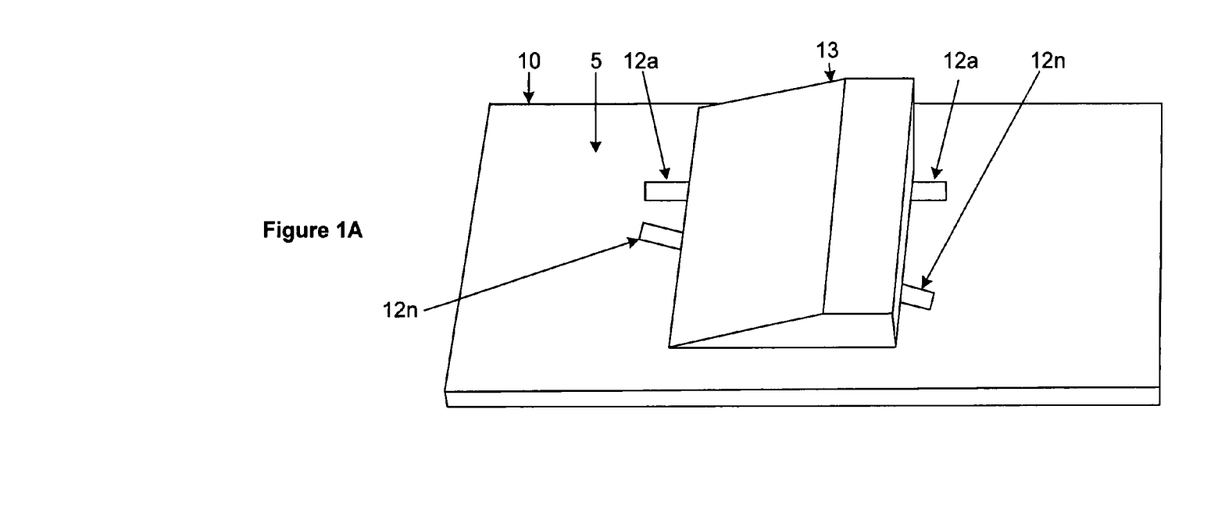
FIG. 1A is a perspective top view of a platform showing examples of attachments and a support object.

As shown in FIG. 1, a radiolucent platform 10 is shaped to accommodate at least a portion of the lower body of a patient during medical imaging. The width of the platform 10 is made to fit within the inner diameter of a patient aperture of a medical imager, such as, but not limited to, CT, MRI, x-ray, fluoroscopy, and ultrasound devices. The length of the platform 10 accommodates pediatric to adult patients. In one embodiment, the platform 10 comprises an extendable portion 11. The extendible portion 11 is used to accommodate larger patients. Alternatively, as shown in FIG. 1A, the platform 10 is sized to accommodate small, medium and large patients.

The platform 10 is of sufficient length to support a patient's lower back, buttocks, legs, and feet when the patient is placed on the platform, such as, but not limited to, in a supine position with legs extended. The platform 10 is of sufficient thickness to provide support and sufficient thinness to maximize allowable space within the imager and remain relatively lightweight. The platform 10 may be covered and/or padded. The covering and padding may comprise the entire platform 10 or portions of the platform and may be removable. In one embodiment, the padding comprises a filler, such as foam, textile, air, or the like. In an alternative embodiment, the platform 10, at the point of contact with a patient's back, comprises an incline, depression, cutout area, or other similar features shaped to accommodate the patient comfortably.

The platform 10 comprises an attachment for releasably securing 12a, 12n support objects to the platform 10. Any number of attachments 12a, 12n may be used. In an embodiment, as shown in FIG. 1, the attachment 12a, 12n is located essentially parallel to and at a distance from an edge of the length of the platform 10, however, other placement arrangements are equally useable. The attachment 12a, 12n may extend the length of the platform 10, and may also extend the length of extendable portion 11. Alternatively, the attachment 12a, 12n is located at predetermined site(s) on the platform 10 and/or extendable portion 11.

Figure 2:
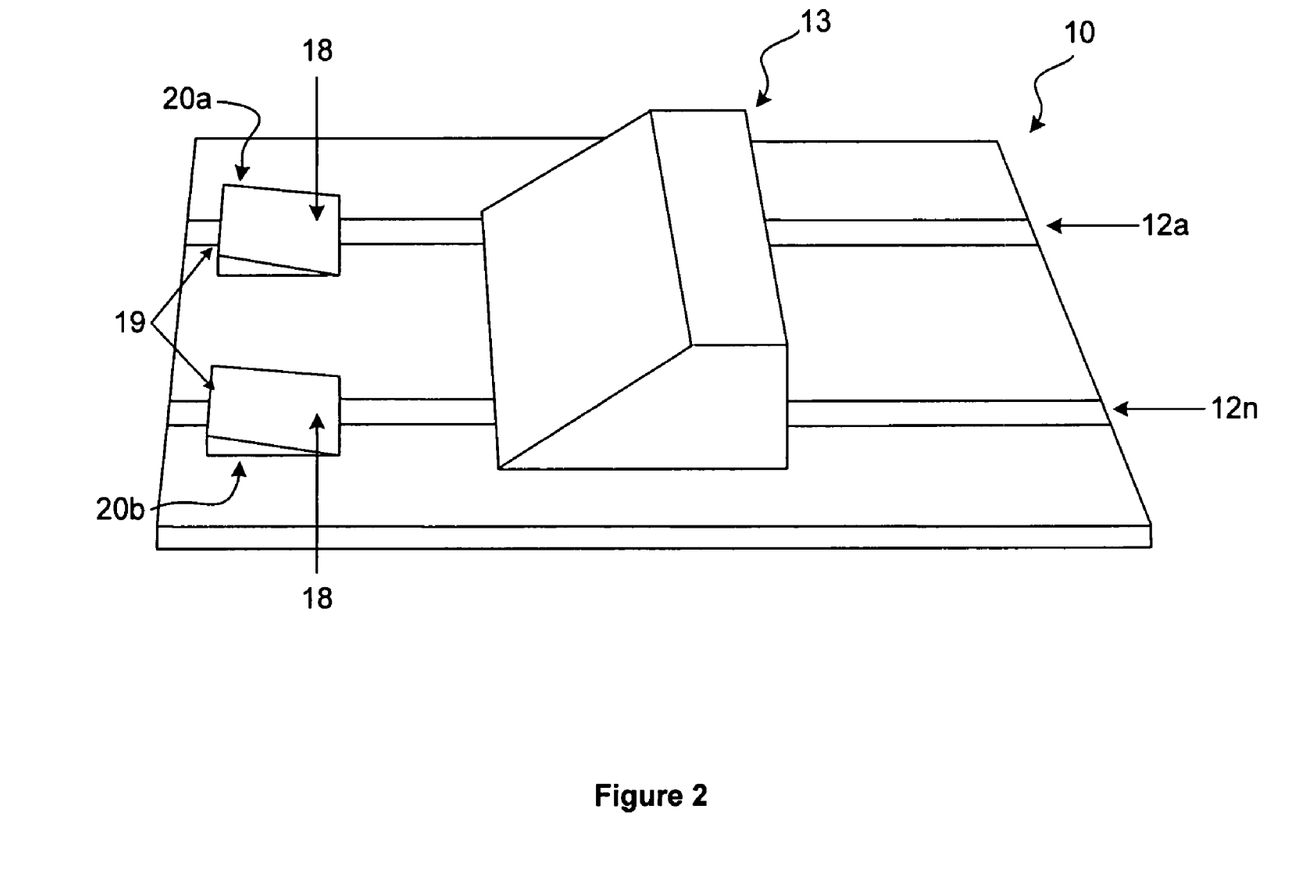
FIG. 2 is a perspective top view of a platform with a knee support and two foot supports attached.

In one embodiment, the attachment 12a, 12n is at least one face of a hook and loop fastener attached to the platform 10. Two hook and loop fasteners may be arranged in a generally parallel relationship, which may extend the length of the platform as shown in FIG. 1. The hook and loop fasteners in the embodiment illustrated in FIG. 2 are at least 2 inches wide. Those skilled in the art will appreciate other quantities, sizes and shapes of means for releasably attaching given the present disclosure. Other examples of attachments 12a, 12n are zippers, pins, snaps, hooks, eyes, buckles, ties, buttons, buttonholes, and the like.

Figure 3A:
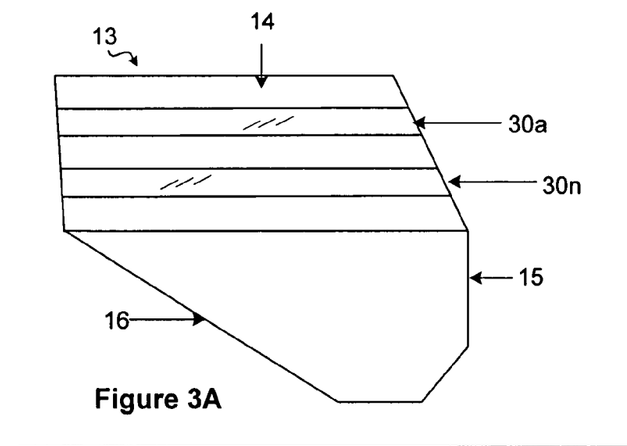
FIG. 3A is a perspective bottom view of an example knee support showing a fastener.
Figure 3B:
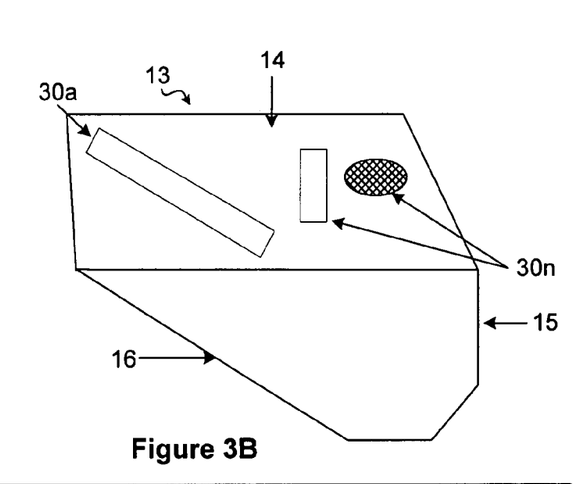
FIG. 3B is a perspective bottom view of a knee support showing examples of fasteners.
Figure 3C:
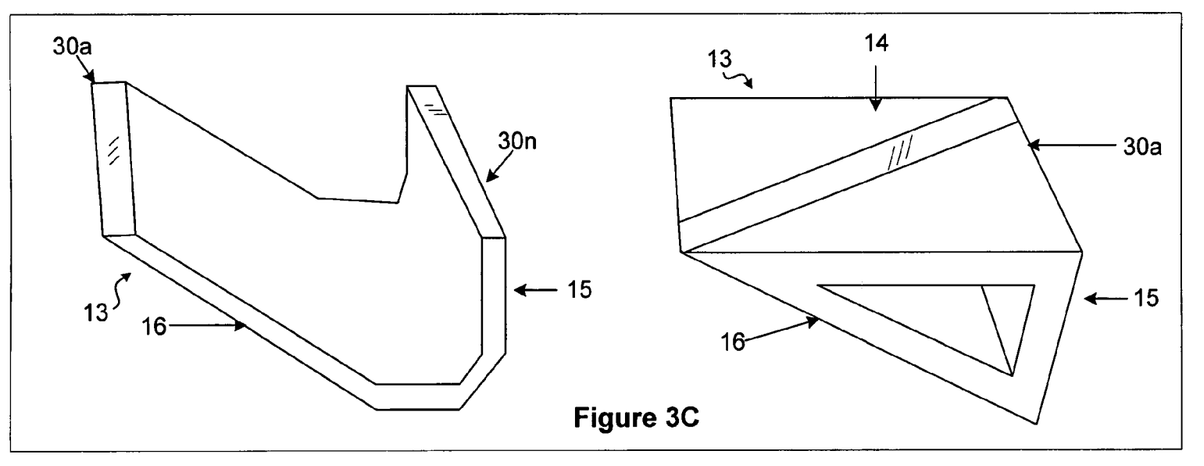
FIG. 3C is a perspective bottom view of alternate knee support embodiments with additional examples of fasteners.

Support objects that are attached to the platform 10 may include a knee support 13. The knee support is attachable to the attachment 12a, 12n at any point on the platform 10. In one embodiment, the knee support 13 is a shape enclosed in a wipeable covering, for example, a plastic or textile. The knee support 13 may be filled with anything that is radiotranslucent, such as plastic, textile, air, or the like. In an embodiment, the knee support 13 may also comprise a hollow shape, such as illustrated in FIG. 3C. The knee support 13 has a knee bottom surface 14, as shown in FIGS. 3A–C, that is in an essentially parallel plane to an upper surface 5 of the platform 10 when the knee support 13 is placed on the platform 10. The knee support 13 has a knee first surface 16 and a knee second surface 15, both of which intersect with the knee bottom surface 14 such that, when a patient is positioned on the knee support 13, one or both of the patient's calves are supported by the first surface 16 to obtain the desired position for imaging at least one of the patient's lower extremities.

In an embodiment, the knee first surface 16 intersects with the knee bottom surface 14 at an angle of about 45° and the knee second surface 15 intersects with the knee bottom surface 14 at an angle of about 90°. The knee support 13 may comprise additional surfaces, and may alternately comprise a curvilinear shape. The knee support 13 may be sized to accommodate a wide range of patients.

FIG. 3A shows a knee bottom surface 14 with a knee support fastener 30a, 30n compatible with the attachment 12a, 12n. As shown as examples in FIGS. 3A–3C, any number, shape, placement and configuration of knee support fastener 30a, 30n may be used separately or in combination. The knee support fastener 30a, 30n may be securely positioned at a plurality of points on the platform 10.

In an embodiment illustrated in FIG. 3A, the knee support fastener 30a, 30n is located essentially parallel to and at a distance from an edge of the length of the knee bottom surface 14. The knee support fastener 30a, 30n may extend the length of the knee bottom surface 14. Alternatively, the knee support fastener 30a, 30n is located at predetermined site(s) on the knee bottom surface 14.

As illustrated in FIG. 3A and FIG. 3C, the knee support fastener 30a, 30n may comprise at least one face of a hook and loop fastener attached to knee bottom surface 14. Two hook and loop fasteners may be arranged in a generally parallel relationship extending the length of the knee bottom surface 14. In the embodiment illustrated in FIG. 3A, the hook and loop fasteners are at least 2 inches wide. Those skilled in the art will appreciate other quantities, sizes and shapes of means for detachably attaching the knee support given the present disclosure. Other examples of knee support fasteners 30a, 30n are zippers, pins, snaps, hooks, eyes, buckles, ties, buttons, buttonholes, and the like.

Alternatively, as shown in FIG. 3C, the knee support 13 may comprise a partial bottom surface with knee support fastener 30a, 30n. In this embodiment, the knee support 13 comprises a rigid radiotranslucent material, which may be padded and/or covered.

As shown in FIG. 2, the support object may comprise one or more than one detachable moveable foot support 20a, 20b attached to the platform 10 by the attachment 12a, 12n. The foot support 20a, 20b comprises a radiotranslucent material such as plastic, textile, air, or the like, and may be enclosed in a radiotranslucent covering. For example, the foot support 20a, 20b may be a foam covered with a wipeable covering. The foot support 20a, 20b may also comprise a hollow shape, such as illustrated in FIG. 3E.

Figure 3D:
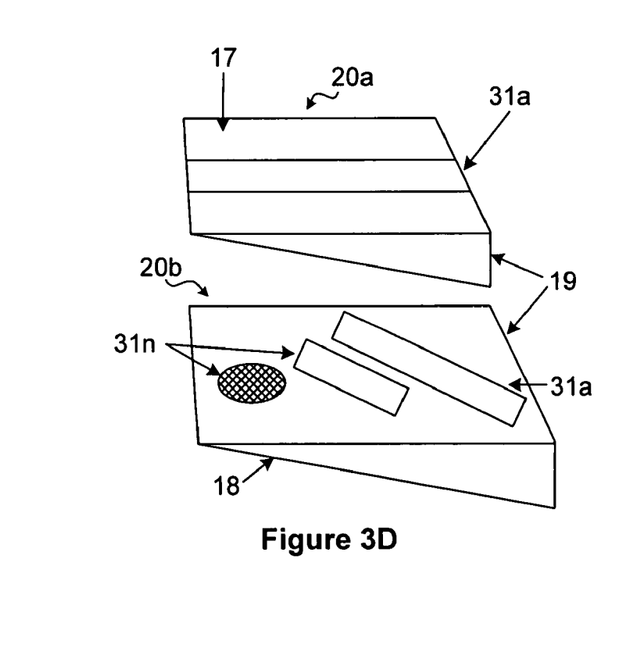
FIG. 3D is a perspective bottom view of two foot supports showing examples of foot support fasteners.
Figure 3E:
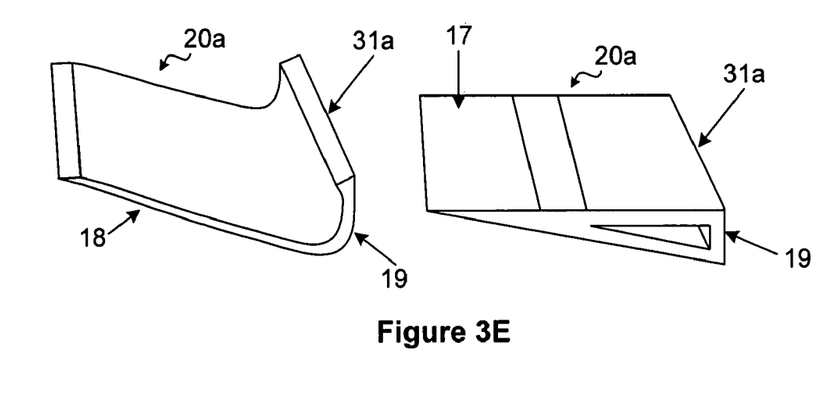
FIG. 3E is a perspective bottom view of alternate foot support embodiments showing additional examples of foot support fasteners.
Figure 3F:
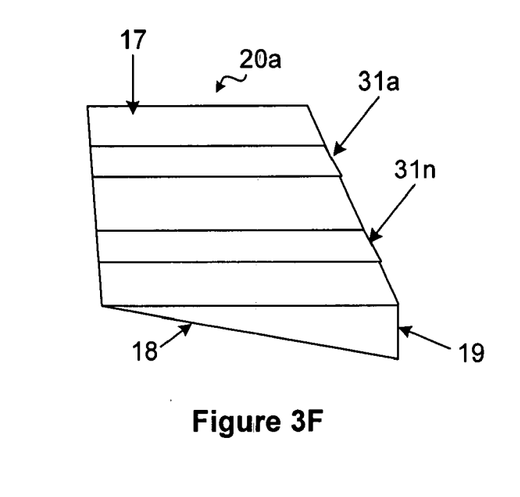
FIG. 3F is a perspective bottom view of an alternate foot support embodiment.

In an embodiment shown in FIG. 3D, the foot support 20a, 20b has a foot bottom surface 17 that is essentially parallel to the platform 10 when the foot support 20a, 20b is placed on the upper surface 5 of the platform 10. The foot support 20a, 20b may be shaped to support both feet of a patient, as illustrated in FIG. 3F, or may be shaped to support an individual foot. Two single foot supports 20a, 20b may be used together to position both feet, or alone to position one foot.

The foot support 20a, 20b comprises a foot first surface 18 and a foot second surface 19. In an embodiment illustrated in FIG. 3D, the foot first surface 18 intersects the foot bottom surface 17 at an angle of about 45° or less, and the foot second surface 19 intersects the foot bottom surface 17 at an angle of about 90°. The one or more than one foot support 20a, 20b may comprise additional surfaces, and may alternately comprise a curvilinear shape. The one or more than one foot support 20a, 20b may be sized to accommodate a wide range of patients.

As shown in FIG. 3D, the foot bottom surface 17 comprises a foot support fastener 31a, 31n compatible with the attachment 12a, 12n. When the foot support 20a, 20b is attached to the attachment 12a, 12n on the upper surface 5 of the platform 10, the foot support bottom surface 17 and the platform upper surface 5 form essentially parallel planes. Any number, shape, placement, and configuration of means for detachably attaching the foot support 20a, 20n may be used separately or in combination. The foot support fastener 31a, 31n cooperates with the attachment 12a, 12n such that the foot support 20a, 20b may be securely positioned at a plurality of points on the platform 10.

As shown in FIG. 3E, the foot support 20a, 20b may comprise a partial bottom surface with foot support fastener 31a, 31n. In this embodiment, a relatively rigid radiotranslucent material is used for the foot support 20a, 20b, which may be padded or covered.

In an embodiment shown in FIG. 3D, the foot support fastener 31a, 31n is at least one face of a hook and loop fastener. A first foot support 20a with a first hook and loop fastener is located and attached to a first corresponding hook and loop fastener, and a second foot support 20b with a second hook and loop fastener may be located and attached to the first corresponding fastener or may be attached to a second corresponding fastener. The foot support 20a, 20b is positioned on the platform 10 to accommodate and support the feet of a patient during imaging. The patient may be positioned with legs extended or with one or both knees bent.

Figure 4A:
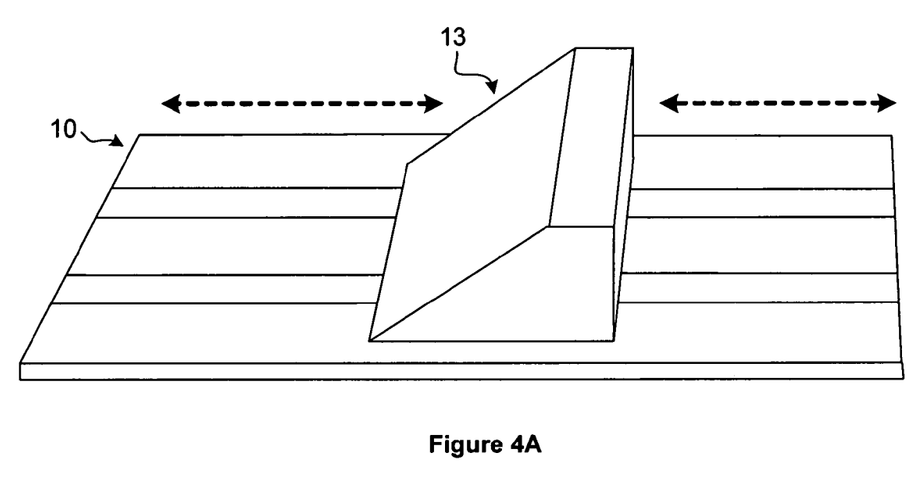
FIG. 4A is a perspective top view showing alternative placement locations of a knee support on a platform.
Figure 4B:
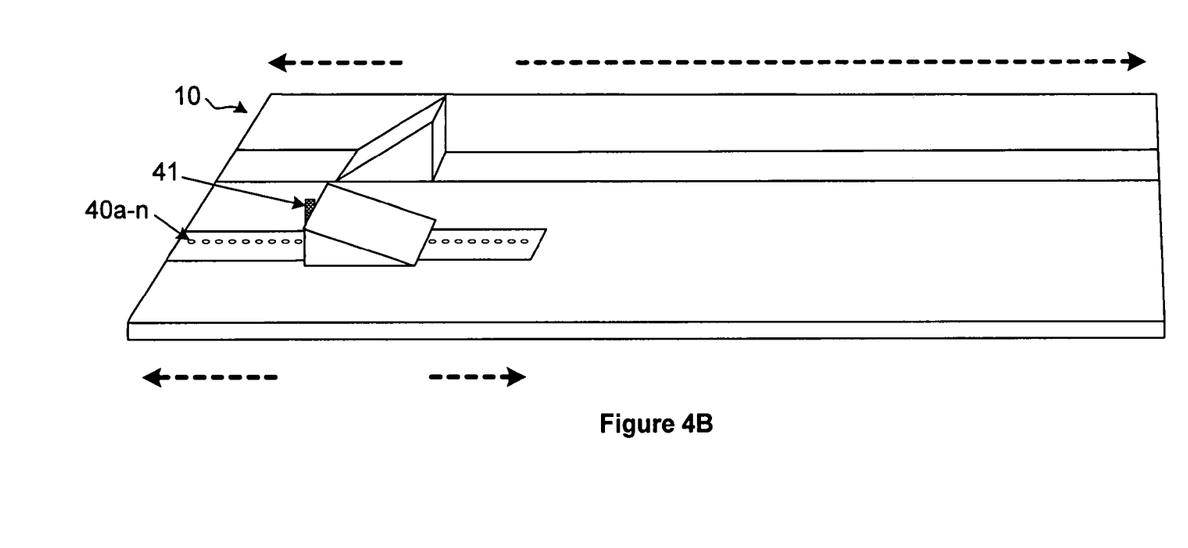
FIG. 4B is a perspective top view showing alternative placement locations of a foot support and an example of means for additional securing.

As shown in FIG. 4B, the foot support 20a, 20b may be positioned and attached to the platform 10 with either the foot first surface 18 or the foot second surface 19 adjacent to the patient's foot. If two foot supports 20a, 20b are used, they may be positioned with the same surface adjacent to the patient's foot, or with different surfaces adjacent to the patient's foot.

FIGS. 4A and 4B show possible positioning of the knee support 13 and the one or more than one foot support 20a, 20b to the attachment 12a, 12n. The movement of support objects 13, 20a, 20b allows placement and support of a patient's lower extremity in the desired position for imaging.

As shown in FIG. 4B, additional securing means 40a–n, 41, such as moveable pegs corresponding to spaced peg holes, may be used for additional stabilization of any of the support objects 13, 20a, 20b.

The one or more than one detachable moveable foot support 20a, 20b may be attached to the platform 10 solitarily, together, with the knee support 13, or with an additional support object. The one or more than one detachable moveable foot support 20a, 20b and the knee support 13 may use the same attachment 12a, 12n or may use alternate or additional attachments 12a, 12n.

Figures 5, 5A:
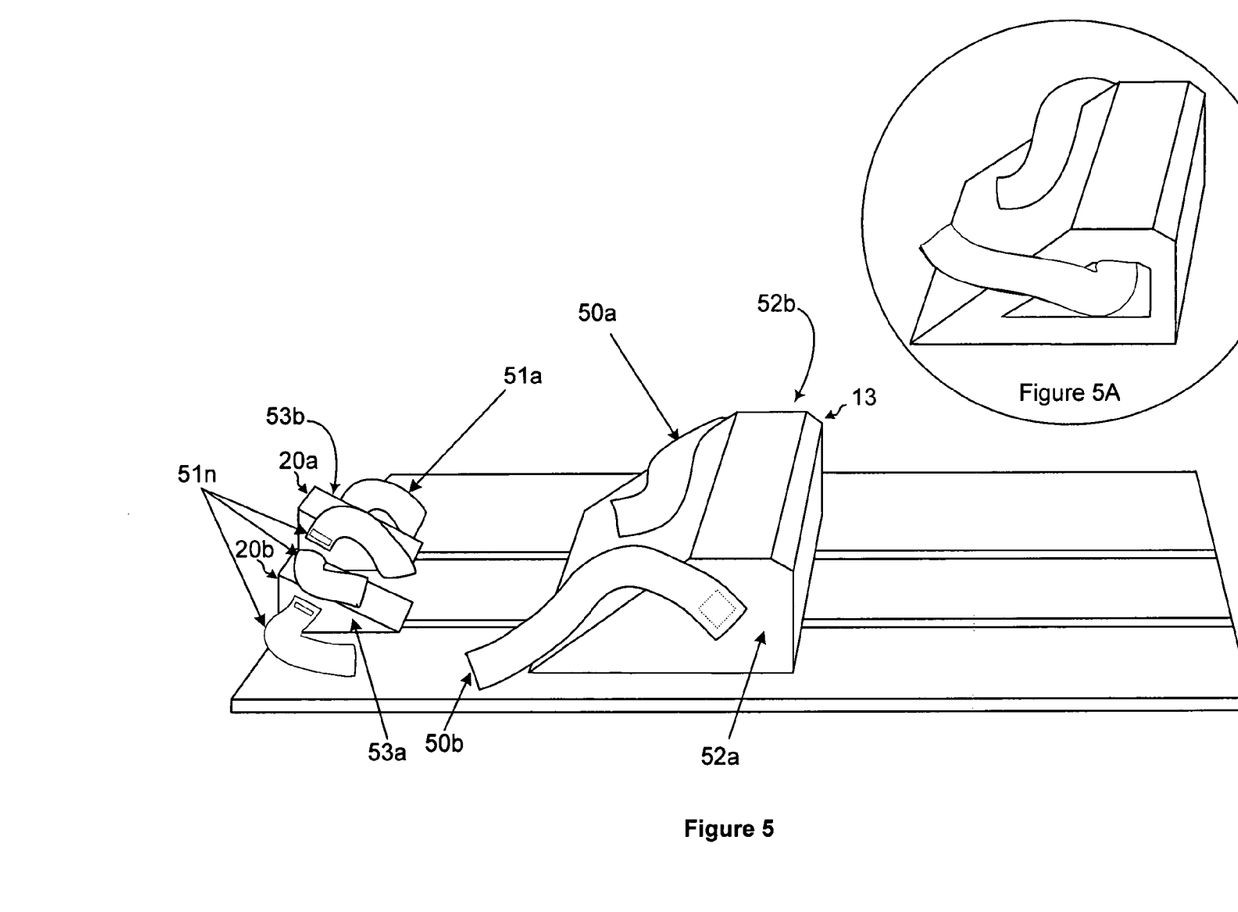
FIG. 5 is a perspective side angle view of a platform with a knee support and two feet supports attached and showing examples of restraints.
FIG. 5A depicts an alternate embodiment showing a hollow knee support with an alternate restraint.

As shown in FIG. 5, the knee support 13 may include a restraint 50a, 50b to assist in holding a patient's legs against the knee support 13. The foot support 20a, 20b may include a restraint 51a–n to assist in holding the patient's foot or feet against the foot support 20a, 20b. The restraint 50a, 50b, 51a–n may be any mechanism to secure the limb or foot. Examples of restraining means include mechanisms that a patient's limb slips through, such as an attached piece with elastic banding, and mechanisms that secure the limb after placement, such as ties, stretchable or non stretchable components that join, and the like.

In an embodiment shown in FIG. 5, the knee support restraint 50a, 50b comprises a hook and loop fastener attached to alternate sides 52a, 52b of the knee support 13. The hook and loop fastener is of sufficient length and width to interlock snugly over one or both legs of a patient to hold the limb(s) stationary. The foot support restraint 51a–n comprises a hook and loop fastener attached to alternate sides 53a, 53b of the foot support 20a, 20b. The foot hook and loop fastener is of sufficient length and width to interlock snugly over the patient's foot when the patient is positioned during imaging. The foot support restraint 51a–n is fastened to the foot support sides 53a, 53b to hold the foot stationary against the foot first surface 18 or to hold the foot stationary against the second surface 19.

In an alternative embodiment, a single foot support 20a may accommodate one or both feet of a patient. The restraint 51a–n is attached to a midpoint of the foot first surface and/or second surface at a midpoint. The restraint 51a–n may cooperate with corresponding restraints 51a–n attached to alternate sides 53a, 53b of the foot support 20a, or may comprise a single piece.

As shown in FIG. 5A, the restraint 50a, 51a may extend through the hollow portion of the support object. Those skilled in the art will appreciate other quantities, sizes, and shapes of restraints given the present disclosure.

Figure 6A:
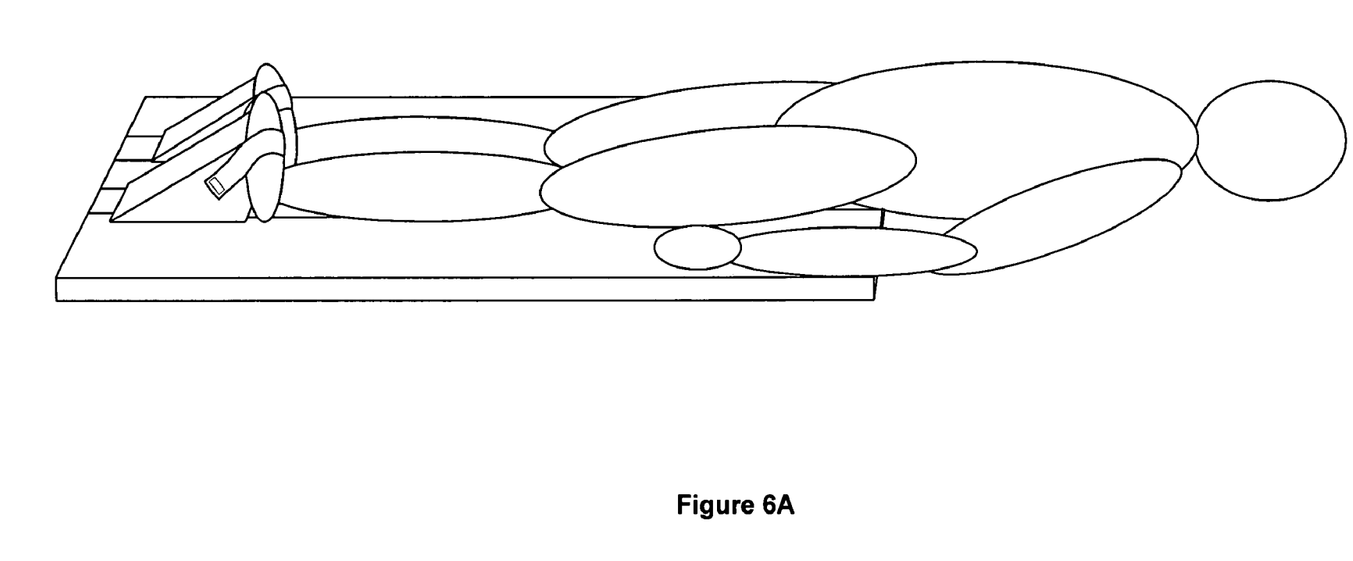
FIG. 6A is a perspective side angle view of patient positioned on a platform with two foot supports.

In an embodiment shown in FIG. 6A, the attachment 12a, 12n comprise two 2" hook and loop fasteners placed essentially parallel to the length of the platform 10. A first foot support 20a is located and attached to a first hook and loop fastener by a corresponding hook and loop fastener secured to the first foot support 20a, and a second foot support 20b is located and attached to a second hook and loop fastener by a corresponding hook and loop fastener secured to the second foot support 20b in respective locations along the platform 10 so that the foot supports 20a, 20b, securely accommodate and support each foot of a patient while the patient is positioned in a supine position with legs extended.

Figure 6B:
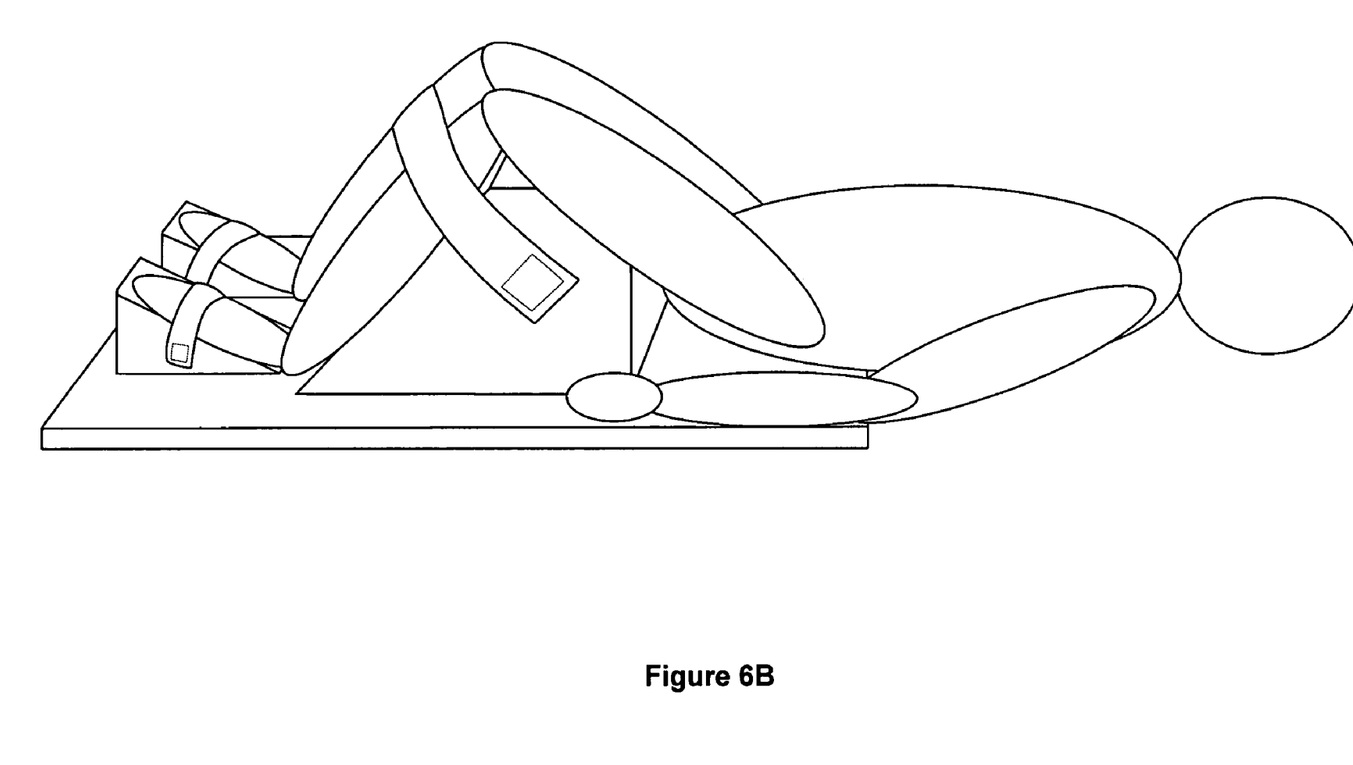
FIG. 6B is a perspective side angle view of a patient positioned on a platform with a knee support and two foot supports.

FIG. 6B shows a patient positioned using an embodiment of the invention comprising a knee support 13 and two foot supports 20a, 20b secured by hook and loop fasteners to the platform 10. The patient's legs are secured to the knee support 13 by a hook and loop fastener and each foot is secured to each foot support 20a, 20b by a hook and loop fastener such that the patient is supported in a predetermined position for imaging at least one extremity.

While the invention is described in some detail with specific reference to certain embodiments and alternatives, there is no intent to limit the invention disclosed to a particular embodiment or specific alternatives. Therefore, the true scope of the invention is defined not by the foregoing description but by the following claims.

What is claimed is:

1. A device for positioning at least one lower extremity of a patient during medical imaging comprising:
   a radiotranslucent platform;
   a radiotranslucent knee support, said knee support comprising a first knee surface and a second knee surface, said first knee surface angled at about 45° with respect to a top surface of the platform and the second knee surface angled at about 90° with respect to the surface of the platform;
   at least one radiotranslucent foot support, said foot support comprising a foot surface, said foot surface at an angle of less than about 45° with respect to the top surface of the platform; and at least one attachment to releasably secure at least one of the knee support and the foot support to the platform, such that at least one lower extremity of a patient is in a predetermined position for medical imaging.

2. The device of claim 1 wherein the foot support and the knee support each comprise a padded rigid material.

3. The device of claim 1 wherein the foot support and the knee support each comprise at least one restraint.

4. The device of claim 3 wherein the restraint is a band, a stretchable band, at least one tie, a joinable stretchable component, or a joinable nonstretchable component.

5. The device of claim 3 wherein the restraint comprises a hook and loop fastener.

6. The device of claim 1 wherein the foot support and the knee support each comprise at least one fastener corresponding with the attachment.

7. The device of claim 6 wherein the fastener comprises a hook and loop fastener.

8. The device of claim 1 wherein the attachment is a zipper, pin, snap, hook, eye, buckle, tie, button, buttonhole, or hook and loop fastener.

9. The device of claim 1 wherein the attachment is a first hook and loop fastener and a second hook and loop fastener, each extending a length of the platform.

10. The device of claim 1 wherein one foot support supports and restrains both feet of the patient.

11. The device of claim 1 comprising additional means for securing one or more than one support selected from the group consisting of the knee support and one or more than one foot support.

12. The device of claim 11 wherein the additional securing means is at least one peg corresponding to at least one peg hole in the platform.

13. The device of claim 1 wherein the platform comprises an extendable portion.

14. The device of claim 1 wherein the platform is enclosed in a radiotranslucent covering.

15. The device of claim 1 wherein the knee and foot supports are each enclosed in a radiotranslucent covering.

16. The device of claim 1 wherein the knee and foot supports are each a shape filled with a foam, textile, or air.

17. A device for positioning at least one lower extremity of a patient during medical imaging comprising:

a radiotranslucent platform with a removeable radiotranslucent platform covering;

a radiotranslucent knee support with at least one knee restraint and a removeable radiotranslucent knee support covering, said knee support comprising a first knee surface and a second knee surface, said first knee surface angled at about 45° with respect to a top surface of the platform and the second knee surface angled at about 90° with respect to the surface of the platform;

one or more than one radiotranslucent foot support with at least one foot restraint and a removeable radiotranslucent foot support covering, wherein said foot support comprises a first foot surface and a second foot surface, said first foot surface at an angle of less than about 45° with respect to the top surface of the platform and the second foot surface at an angle of about 90° with respect to the surface of the platform;

at least one attachment to releasably secure one of the knee support and one or more foot support to the platform, such that at least one lower extremity of a patient is in a predetermined position for medical imaging.

* * * * *